United States Patent [19]

Theeuwes et al.

[11] Patent Number: 5,045,059
[45] Date of Patent: * Sep. 3, 1991

[54] INTRAVENOUS SYSTEM FOR DELIVERING A BENEFICIAL AGENT

[75] Inventors: Felix Theeuwes; Su I. Yum, both of Los Altos, Calif.

[73] Assignee: Alza Corporation, Palo Alto, Calif.

[*] Notice: The portion of the term of this patent subsequent to Jan. 15, 2008 has been disclaimed.

[21] Appl. No.: 568,457

[22] Filed: Aug. 15, 1990

Related U.S. Application Data

[62] Division of Ser. No. 311,906, Feb. 15, 1989, Pat. No. 4,969,871.

[51] Int. Cl.$^5$ .................................................. A61M 37/00
[52] U.S. Cl. ................................... 604/82; 604/80; 604/890.1; 604/83
[58] Field of Search .................................. 604/80-85, 604/890.1, 892.1

[56] References Cited

U.S. PATENT DOCUMENTS

| | | | |
|---|---|---|---|
| 3,536,809 | 10/1970 | Applezweig | 424/28 |
| 3,598,122 | 8/1971 | Zaffaroni | 128/268 |
| 3,598,123 | 10/1971 | Zaffaroni | 128/268 |
| 3,699,963 | 10/1972 | Zaffaroni | 128/268 |
| 3,731,683 | 5/1973 | Zaffaroni | 128/268 |
| 3,734,097 | 5/1973 | Zaffaroni | 128/268 |
| 3,742,951 | 7/1973 | Zaffaroni | 128/268 |
| 3,787,571 | 1/1974 | Higuchi | 424/239 |
| 3,797,494 | 3/1974 | Zaffaroni | 128/268 |
| 3,964,482 | 6/1976 | Gerstel et al. | 128/260 |
| 3,996,934 | 12/1976 | Zaffaroni | 128/268 |
| 4,031,894 | 6/1977 | Urquhart et al. | 128/268 |
| 4,060,084 | 11/1977 | Chandrasekaran et al. | 128/260 |
| 4,144,317 | 3/1979 | Higuchi et al. | 424/21 |
| 4,439,183 | 3/1984 | Theeuwes | 604/85 |
| 4,511,353 | 4/1985 | Theuwes | 604/85 |
| 4,533,348 | 8/1985 | Wolfe et al. | 604/85 |
| 4,534,757 | 8/1985 | Geller | 604/85 |
| 4,740,103 | 4/1988 | Theeuwes | 604/83 |
| 4,740,197 | 4/1988 | Theeuwes | 604/84 |
| 4,740,200 | 4/1988 | Theeuwes | 604/85 |
| 4,740,201 | 4/1988 | Theeuwes | 604/84 |
| 4,741,734 | 5/1988 | Theeuwes | 604/84 |
| 4,857,052 | 8/1989 | Theeuwes | 604/83 |
| 4,871,352 | 10/1989 | Tran | 604/82 |

FOREIGN PATENT DOCUMENTS

WO8404036 10/1984 World Int. Prop. O. .

OTHER PUBLICATIONS

J. Pharma Sci. vol. 52, pp. 1145–1149 (1963).
J. Pharma Sci. vol. 53, pp. 798–802, (1964).
J. Pharma Sci. vol. 54, pp. 1459–1464 (1985).
J. Pharma Sci. vol., 55, pp. 840–843, and 1224–1239 (1966).
Encyl. Polymer Sci. Techol., vols. 5 and 9, pp. 65–82 and pp. 794–807, (1986).

Primary Examiner—Stephen C. Pellegrino
Assistant Examiner—Michael Refa
Attorney, Agent, or Firm—D. Byron Miller; Edward L. Mandell; Steven F. Stone

[57] ABSTRACT

A drug formulation chamber for an intravenous administration set is provided. The intravenous administration set includes a container of an IV fluid, a drip chamber, a drug formulation chamber, and an adapter-needle assembly. The drug formulation chamber has a fluid inlet and a fluid outlet for maintaining a flow of IV fluid through the chamber. A portion of the chamber wall is comprised of a window material which allows the drug to diffuse therethrough but which prevents convective loss of the IV fluid. A flow distributor is provided within the chamber for distributing the flow of IV fluid along the interior surface of the window. A transdermal-type drug delivery device is adhered to the exterior surface of the window. Drug is delivered by the delivery device through the window and into the flowing IV fluid. The device delivers drug into the IV fluid at a rate that is independent of the flow rate of IV fluid through the formulation chamber. The rate of drug delivery from the device into the IV fluid is controlled by either the window itself or by a membrane layer in the drug delivery device. A plurality of drug delivery devices may be adhered to the window to deliver a plurality of drugs or to deliver a single drug at a higher dosage rate. A similar window may be placed in an IV bag to deliver a drug into the IV fluid therein.

21 Claims, 1 Drawing Sheet

INTRAVENOUS SYSTEM FOR DELIVERING A BENEFICIAL AGENT

CROSS-REFERENCE TO RELATED APPLICATIONS

This application is a division of U.S. Pat. Application Ser. No. 07/311,906 filed on Feb. 15, 1989, U.S. Pat. No. 4,969,871. This application is copending with U.S. Pat. Application Ser. No. 07/311,905, filed on Feb. 15, 1989, U.S. Pat. No. 4,985,016, entitled "INTRAVENOUS SYSTEM FOR DELIVERING A BENEFICIAL AGENT" (ARC 1486) and assigned to ALZA Corporation of Palo Alto, CA.

BACKGROUND OF THE INVENTION

1. Field of the Invention

This invention pertains to a parenteral drug delivery system, and to a drug formulation chamber in combination with a drug delivery device. The invention relates also to a method of parenterally (e.g., intravenously) administering a drug, and to a method of formulating the drug during parenteral administration.

2. Description of the Prior Art

The parenteral administration of medical liquids is an established clinical practice. The liquids are administered particularly intravenously, and the practice is used extensively as an integral part of the daily treatment of medical and surgical patients. The liquids commonly administered include blood and blood substitutes, dextrose solutions, electrolyte solutions and saline. Generally the liquids are administered from an intravenous (IV) delivery system having a container suspended above the patient, with the liquid flowing through a catheter hypodermic needle set to the patient.

The administration of liquids intravenously is a valuable and important practice that contributes to the optimal care of the patient. However, it does not easily provide a satisfactory means and method for administering concomitantly therewith a beneficial agent, such as a drug. In the past, beneficial agents have been administered intravenously by one of the following methods (1) temporarily removing or disconnecting the IV system administering the agent to the patient, then administering the drug by hypodermic injection (either into the disconnected IV line or directly into the vein of the patient), followed by reinserting the IV system into the patient; (2) adding the agent to the IV liquid in the container which is then carried by the flow of the liquid to the patient; (3) adding the agent to an IV liquid in a secondary container (called a partial fill) that is then connected to the primary IV line; (4) adding the agent to an IV liquid contained in a piggyback vial which is subsequently connected to the primary IV line; or (5) administering intravenously an IV liquid containing a beneficial agent using a pump. While these techniques are used, they have major disadvantages. For example, they often require preformulation of the agent medication by the hospital pharmacist or nurse. They often require separate connections for joining the drug flow line to the primary intravenous line which further complicates intravenous administration. The use of certain types of pumps (e.g., reciprocating pumps) can produce pressures that can vary at the delivery site. Finally, the rate of agent delivery to the patient often is unknown as it is not rate-controlled agent delivery but rather is dependent on the rate of IV fluid flow.

In response to these difficulties, Theeuwes in U.S. Pat. No. 4,511,353 (and in related U.S. Pat. Nos. 4,740,103; 4,740,200 and 4,740,201) developed a formulation chamber adapted to easily fit into a conventional IV administration set. The formulation chamber is adapted to contain a drug delivery device for delivering a drug or other beneficial agent into the IV fluid flowing through the formulation chamber. The drug delivery device within the formulation chamber is selected from osmotic pumps (FIGS. 2a, 2b, 9, 10, and 11), release rate controlling membranes surrounding a drug reservoir (FIGS. 3-5), rate-controlled delivery reservoirs within a pocket in the drug formulation chamber, the pocket formed by a permeable membrane or screen/mesh which allows passage of both IV fluid and drug solution therethrough (FIGS. 12 and 13) and polymer matrices containing the drug, the drug being able to diffuse through the matrix into the flowing IV fluid (FIGS. 6-8). All of these devices provide the advantage of controlling the rate at which the drug or other beneficial agent is released into the IV fluid, independently of the rate at which the IV fluid flows through the formulation chamber. Unfortunately, the drug delivery systems disclosed in these patents do not allow a medical technician to quickly and easily change the type of beneficial agent being delivered into the flowing IV fluid or to quickly and easily change the delivery rate of the beneficial agent so delivered. In order to change the type of agent delivered or the agent delivery rate with the delivery systems disclosed in these patents, it is necessary to completely disassemble the drug formulation chamber and replace the rate-controlled drug delivery device within the chamber. Unfortunately, when the drug formulation chamber is disassembled, there is a break in the sterile field which can lead to patient infection and therefore necessitates re-sterilizing the entire apparatus.

Thus, there remains a need for a drug formulation chamber which can deliver one or more beneficial agents, such as a drug, into an IV fluid flowing in a standard IV administration set and which can quickly and easily change the type and/or change the delivery rate of beneficial agent so delivered without contaminating the sterile field.

Accordingly, it is an object of this invention to provide a parenteral (e.g., intravenous) delivery system which delivers an agent at a controlled rate into a flowing parenteral fluid for optimizing the care of an animal (e.g., a human) whose prognosis benefits from parenteral delivery.

It is another object of the invention to provide an intravenous delivery system having an agent formulation chamber which is adapted to be used with a drug delivery device for admitting a drug or other beneficial agent at a rate controlled by either the drug delivery device, the formulation chamber, or both, instead of by the flow rate of intravenous fluid through the system, for optimizing the care of a patient on intravenous delivery.

Another object of the invention is to provide an intravenous delivery system having an agent formulation chamber which is adapted to be used with a transdermal-type drug delivery device which can deliver one or more beneficial agents, such as a drug, into an IV fluid flowing through the formulation chamber and which can quickly and easily change the type and/or change the delivery rate of beneficial agent so delivered without contaminating the sterile conditions within the drug formulation chamber.

A further object of the invention is to provide an intravenous therapeutic system including a container of an intravenous medical fluid and a drug formulation chamber in combination with a drug delivery device which can deliver drug, to a flowing IV fluid, at a rate which is variable and which is accurately controlled by the components of the system.

SUMMARY OF THE INVENTION

Parenteral administration system and a method for the controlled parenteral administration of a beneficial agent to an animal. The agent formulator comprises a chamber having fluid inlet and fluid outlet means to maintain a continuous flow of a parenterally acceptable fluid therethrough. The chamber has a wall portion that is permeable to a beneficial agent to be delivered into the fluid. The beneficial agent should be soluble in the parenteral fluid to enable the agent to diffuse through the wall portion. A flow distributor is provided within the chamber for distributing the flow of parenteral fluid along an interior surface of the wall portion. An agent delivery device is releasably attached to an easily accessible exterior surface of the wall portion. The delivery device includes a reservoir containing the beneficial agent to be delivered into the parenteral fluid. Preferably, the delivery device is a transdermal type drug delivery device comprising a laminate including a backing member, a middle reservoir containing the beneficial agent and an adhesive surface adapted to releasably adhere to the exterior surface of the wall portion. Most preferably, the agent delivery device also includes a rate controlling membrane which controls the rate at which the agent is delivered through the wall portion.

In operation, the fluid flowing through the chamber is distributed by the flow distributor along the interior surface of the wall portion, thereby causing the agent to diffuse from the device through the wall portion and into the flowing fluid. The agent is delivered at a rate that is controlled substantially by the formulator and which is substantially independent of the volumetric flow rate of the fluid flowing through the chamber.

The present invention also provides a parenteral delivery system for administering an agent parenterally to an animal. The system comprises in combination, a container of a pharmaceutically acceptable parenteral fluid that is a carrier for the agent and a parenteral fluid administration set. The administration set is connected to the container for permitting the fluid to flow from the container through the administration set to the animal. The administration set comprises a drip chamber, tubing extending from the drip chamber to the animal, and an agent formulator connected into the tubing such that the intravenous fluid flows through the formulator. The formulator includes a chamber having fluid inlet and outlet means to maintain a continuous flow of the parenteral fluid therethrough. The chamber has a wall portion that is permeable to a beneficial agent to be delivered into the fluid. The beneficial agent should be soluble in the parenteral fluid to enable the agent to diffuse through the wall portion. A flow distributor is provided within the chamber for distributing the flow of parenteral fluid along an interior surface of the wall portion. The formulator also includes an agent delivery device releasably attached to an easily accessible external surface of the wall portion. The delivery device includes a reservoir containing the beneficial agent to be delivered. Preferably, the delivery device is a transdermal drug delivery device comprising a laminate including a backing member, a middle reservoir containing the beneficial agent and an adhesive surface adapted to releasably adhere to the external surface of the wall portion. Most preferably, the agent delivery device includes a rate controlling membrane which controls the rate at which the agent is delivered through the wall portion.

In operation, the fluid flowing through the chamber is distributed by the flow distributor along the internal surface of the wall portion, causing the agent to diffuse from the device through the wall portion and into the flowing fluid. The agent is delivered at a rate which is controlled substantially by the formulator and which is substantially independent of the volumetric flow rate of the fluid flowing through the chamber.

The present invention further provides a method for the controlled parenteral administration of a beneficial agent, such as a drug, to an animal, such as a human. The method comprises the steps of allowing a pharmaceutically acceptable parenteral fluid, which is a carrier for the agent, to flow through an agent formulation chamber. The chamber has an inlet communicating with a container of the parenteral fluid and an outlet communicating with the animal. The chamber also has a wall portion that is permeable to the agent and prevents convective flow of parenteral fluid therethrough. The method further comprises the steps of distributing the flow of parenteral fluid along an interior surface of the wall portion and releasably attaching an agent delivery device to an accessible exterior surface of the wall portion.

The delivery device includes a reservoir containing the beneficial agent to be delivered. Preferably, the delivery device is a transdermal drug delivery device comprising a laminate including a backing member, a middle reservoir containing the beneficial agent and an adhesive surface adapted to releasably adhere to the external surface of the wall portion. Most preferably, the agent delivery device includes a rate controlling membrane which controls the rate at which the agent is delivered through the wall portion.

In operation, the fluid flowing through the chamber is distributed along the interior surface of the wall portion, causing the agent to diffuse from the device through the wall portion and into the flowing fluid. The agent is released at a rate which is controlled substantially by the delivery device and which is substantially independent of the volumetric flow rate of the fluid flowing through the chamber. The method is effective to administer the drug/agent to the animal in a beneficially effective amount over a prolonged period of time.

BRIEF DESCRIPTION OF THE DRAWINGS

In the specification and the drawings, like parts in related Figures are identified by like numbers.

DETAILED DESCRIPTION OF THE INVENTION

Figure 1:
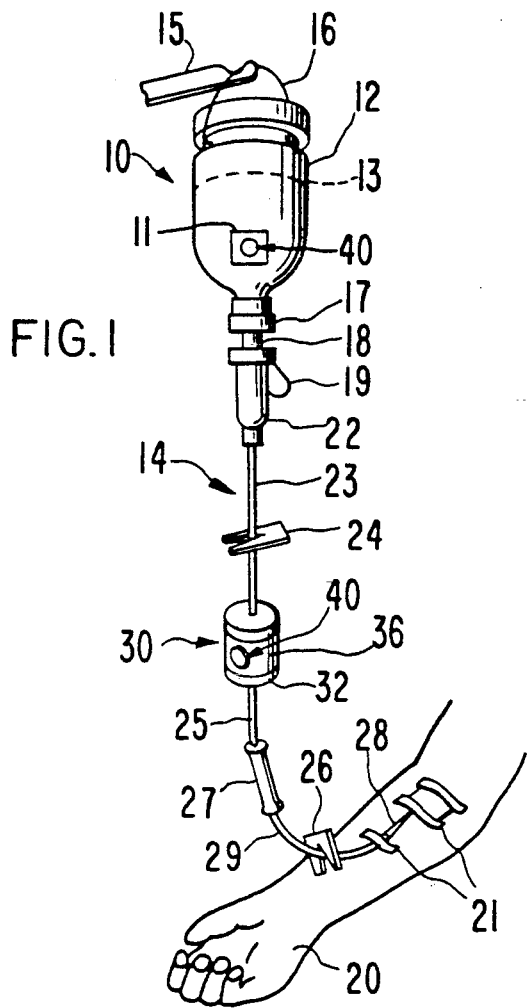
FIG. 1 is a perspective view showing an agent formulator 30 and its use within an intravenous delivery system 10.

FIG. 1 illustrates an operative intravenous delivery system, generally designated by the numeral 10, showing the positioning of an agent formulator 30 therein. System 10 comprises a container 12 that contains a fluid 13 suitable for intravenous administration, and an administration set, generally designated 14. The fluid 13 in container 12 will typically be a medical fluid, i.e., a sterile solution such as an aqueous solution of dextrose, saline, and/or electrolytes. Fluid 13 is a vehicle for intravenous administration of a pharmaceutical agent to a recipient. Container 12 is manufactured from glass or plastic, and is preferably of the no air-tube vacuum type and thus it is used with an administration set that has an air inlet filter. Other types of containers such as the air-tube vacuum type, or the non-vented type, can be used for the intended purpose. These alternative containers do not require an air filter in the administration set. Container 12 can be rigid, semi-rigid or flexible in structure, and it is usually adapted to be hung neckdown from a hanger 15 by a handle 16 that connects or surrounds container 12. The neck of container 12 is covered by a closure 17, generally made of rubber and air-tight.

Alternatively, container 12 can take the form of an infusor or a syringe pump (not shown in the Figures), and in particular a portable infusor or syringe pump, of the kind known in this art.

Administration set 14 and container 12 are interconnected by piercing closure 17 with one end of a hollow spike 18 attached to or formed as a part of administration set 14. Spike 18 is equipped with a side air vent 19. The other end of spike 18 is enlarged and fits snugly into a drip chamber 22. Drip chamber 22 traps air contained in the set 14 and facilitates adjusting the flow rate of intravenous fluid 13 from container 12 as the flow proceeds drop wise. The outlet at the bottom of drip chamber 22 is connected to a first segment of tubing 23 which fits into agent formulator 30, the details of which are presented in FIGS. 2 and 3. A second segment of tubing 25 leads from agent formulator 30 to bacterial filter 27. A third segment of tubing 29 extends from filter 27 to an infusion agent receptor site, terminating in an adapter-needle assembly 28 that is inserted into a vein of a warm-blooded animal 20, shown as a human arm. A piece of tape 21 holds adapter-needle assembly 28 firmly in place on the recipient's arm. The administration set can also include a pair of tubing clamps 24 and 26 located on either side of formulator 30 which may be used to govern or stop the flow of intravenous fluid through the intravenous delivery system 10.

In one embodiment of the present invention, a portion of the wall of container 12 is comprised of a material 11 which is permeable to the beneficial agent contained within, and delivered by, the delivery device 40. The wall portion 11 forms a "drug delivery window" within the otherwise impermeable wall of container 12. During delivery of beneficial agent from device 40, the IV fluid 13 must be in contact with the interior surface of wall portion 11. Accordingly, the wall portion 11 is preferably located in a downstream portion of the wall of container 12 most preferably adjacent the neck of container 12.

Figure 2:
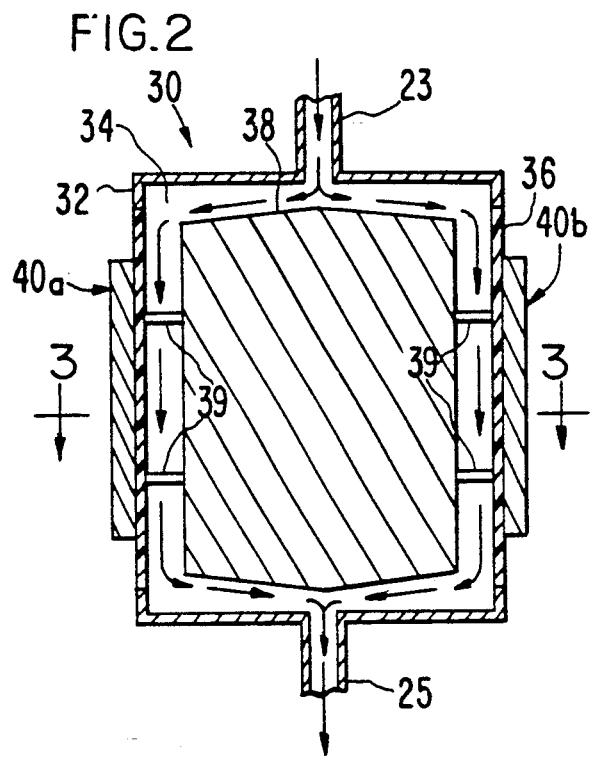
FIG. 2 is a sectional view of one embodiment of an agent formulator according to the present invention.
Figure 3:
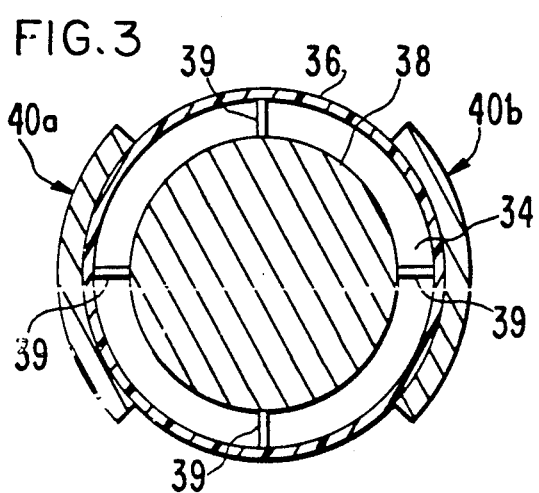
FIG. 3 is a sectional view of the agent formulator illustrated in FIG. 2, taken along line 3—3.

As an alternative to, or in addition to the drug delivery window 11 in container 12, an agent formulator 30 may be provided downstream from the container 12. Agent formulator 30, as seen in FIGS. 2 and 3, comprises a wall 32 forming a chamber 34. At least a portion of the wall 32 is comprised of a material 36 which is permeable to the beneficial agent contained within, and delivered by, the delivery device 40. The wall portion 36 forms a drug delivery window, similar to wall portion 11, within the otherwise impermeable wall 32 which may be formed of glass, plastic or the like.

As best shown in FIGS. 2 and 3, a flow diverter 38 is provided within chamber 34. The flow diverter 38 is secured within chamber 34 by supports 39. Preferably, formulator 30 has a cylindrical shape and the wall portion 36 extends around the entire circumference of formulator 30. The flow diverter 38 also preferably has a roughly cylindrical shape. The entire chamber 34 preferably remains filled with the flowing IV fluid 13 to ensure that the entire interior surface of wall portion 36 is in contact with the flowing IV fluid 13. The flow diverter 38 provides two important functions in the formulator 30 of the present invention. First, the flow diverter 38 diverts the flow of IV fluid in the direction shown by the arrows in FIG. 2, i.e., along the interior surface of wall portion 36. Secondly, the flow diverter 38 minimizes the dead volume within formulator 30. Those skilled in the art will appreciate that the flow diverter 38 forces the IV fluid to flow in a relatively constricted space between the flow diverter 38 and the wall portion 36, thereby enabling a greater percentage of the IV fluid 13 to contact the interior surface of wall portion 36.

The efficiency of drug transfer into the IV fluid 13 is greatly enhanced by the flow diverter 38. Flow diverter 38 creates a higher liquid flow velocity (for any given liquid volumetric flow rate) along the interior surface of wall portion 36 which helps eliminate any stagnant fluid layer. In accordance with well known flow principles, the thickness of the stagnant fluid layer along the walls of chamber 34 decreases as the fluid flow velocity through chamber 34 increases. This creates several beneficial effects. First, there is a trend to reduce the number of air or gas bubbles which might otherwise form on the interior surface of the wall portion 36 and which reduce the effective area of the wall portion through which drug can be transferred into the IV fluid. The higher fluid flow velocity also promotes higher drug transfer rates by maintaining a lower drug concentration in the IV fluid adjacent the wall portion 36.

The wall portions 11 and 36 may be comprised of known drug permeable and/or microporous materials which allow the beneficial agent delivered by device 40 to diffuse therethrough but which prevent convective IV fluid flow therethrough. The composition of wall portions 11 and 36 should be selected in accordance with the type of beneficial agent being delivered by device 40. In general, the wall portions 11 and 36 should be comprised of a polymeric composition that allows a drug or other beneficial agent delivered by device 40 to diffuse through the wall portion and into the interior of container 12 and/or into chamber 34. Representative polymers for forming wall portions 11 and 36 include olefin polymers, vinyl polymers, condensation polymers, addition polymers, rubber polymers and silicone polymers, and in particular, polyethylene, polypropylene, polyvinyl acetate, polyvinyl acetal, polyvinyl chloride, polyamides, polyesters, butadiene rubber, organosilicone polymers and copolymers thereof.

When the device 40 delivers a hydrophilic drug, the wall portions 11 and 36 are preferably comprised of a hydrophilic or microporous material. Examples of suitable hydrophilic materials include polyurethanes, polyvinyl alcohols, polyamides and cellophane. Of these, polyurethanes and cellophane are most preferred. Suitable microporous materials are described below in connection with the delivery of polypeptides, proteins and other macromolecules.

When device 40 delivers a lipophilic drug, the wall portions 11 and 36 are preferably comprised of a lipophilic material. Examples of suitable lipophilic materials include natural rubbers, silicone rubbers, Hytrel®(a thermoplastic polyester elastomer sold by E.I. DuPont de Nemours of Wilmington, Del.), ethylene vinyl acetate (EVA), polyvinyl chloride, and Kraton®(a styrene-butadiene block copolymer u sold by Shell Chemical Co. of Houston, Tex.). Of these, ethylene vinyl acetate copolymers, silicone rubbers and natural rubbers are preferred.

When device 40 delivers a polypeptide, protein or other macromolecule, the wall portions 11 and 36 are preferably comprised of a microporous material The pores in the microporous material will generally have a size of less than about 0.2 microns, and preferably about 0.01 to 0.2 microns. Pores having the above recited size ranges are too small to allow bacterial cells to pass through the pores and can thereby maintain the sterility of the container 12 and/or the chamber 34. In general, microporous materials having pore sizes in the above mentioned range will allow water molecules from the parenteral fluid to diffuse into the membrane. In some cases, the exterior of the wall portions 11 and 36 will feel wet to the touch. However, microporous membranes having the above mentioned pore size ranges will be effective to prevent convective flow losses of water-based parenteral fluids through the wall portions 11 and 36. If necessary or desirable, the microporous wall portions 11 and 36 can be treated with a water non-wetting material to further reduce capillary IV fluid losses through the wall portions 11 and 36. In addition, the delivery device 40 may utilize a carrier which is immiscible in water. In such a case, the beneficial agent is suspended in a water-immiscible fluid carrier (e.g., an oil). When the oil-based carrier enters the pores of the microporous membrane, the pores will repel any water-based parenteral fluid which helps prevent convective losses through the wall portions 11 and 36.

Examples of suitable microporous materials include Celgard®(a microporous polypropylene film sold by Celanese Chemical Co. of Dallas, Tex.) cellophane, glass frits, vycor glass, porous glass and microporous membranes of the type utilized in known elementary osmotic pumps. Of these, porous glass is most preferred.

Selection of polymers for forming wall portions 11 and 36 for the passage of a drug therethrough can be determined by measuring the rate of diffusion through the polymeric wall material. Various techniques can be used to determine the permeability of a homopolymer, copolymer, or terpolymer to the passage of a drug. One method that can be used is to position a film of the polymer, of known thickness, as a barrier between a rapidly stirred, saturated solution of the drug and a rapidly stirred solvent bath (typically water), at a constant temperature, typically 25° C., and periodically measuring the concentration in the drug solution and in the solvent bath. Then, by plotting the drug concentration in the solvent bath versus time, the permeability coefficient, P, of the polymeric film may be determined from Fick's Law of Diffusion. Fick's Law of Diffusion is expressed by the following equation (I):

$$\text{Slope of plot} = (Q_2 - Q_1/t_2 - t_1) = P \, AC/h \quad (I)$$

wherein:
$Q_1$ = cumulative amount of drug in the downstream solvent in micrograms at $t_1$;
$Q_2$ = cumulative amount of drug in solvent in micrograms at $t_2$;
$t_1$ = elapsed time to first sample, i.e., $Q_1$;
$t_2$ = elapsed time to second sample, i.e., $Q_2$;
$A$ = area of film in $cm^2$;
$C$ = concentration of drug in saturated solution; and
$h$ = thickness of film in cm.

By determining the slope of the plot, i.e., $[Q_1 - Q_2/t_1 - t_2]$ and solving the equation using the known or measured values of A, C and h, the permeability coefficient, P, in $cm^2$/time of the film for a given drug is readily determined. The procedures used to determine the rate of release through the polymer can be ascertained easily by standard techniques known to the art as recorded in J. Pharm. Sci., Vol. 52, pp 1145–49, (1963); ibid, Vol. 53, pp 798–802, (1964); ibid, Vol. 54, pp 1459–64, (1965); ibid, Vol., 55, pp 840–43 and 1224–39, (1966); Encyl. Polymer Sci. Technol., Vol. 5 & 9, pp 65–82 and 794–807, (1986); the references cited therein, and the like.

Wall portions 11 and 36 may also optionally contain a plasticizer such as a member selected from the group consisting of phthalate ester, adipate ester, sebacate ester, azelate ester, di-2-ethylhexyl phthalate, butyl phthalyl butyl glycolate, diamyl phthalate, dibutyl succinate, diethylene glycol dipropionate, ethyl phthalyl ethyl glycolate, tributyl citrate, tributyl phosphate, triethylene glycol dibutyrate, glycol monoleate, polyethylene glycol 200; polyethylene glycol 400-ML, diethyl lauramide, oleic and mineral oil, and the like. The amount of plasticizer in wall portions 11 and 36 is from about 5 weight percent (wt. %) to 30 wt. %, or more.

When the wall portions 11 and 36 are comprised of a material having poor rigidity and/or strength, it may be supported by a rigid porous or grid-like polymer structure (not shown in the figures) provided within the container 12 or within chamber 34. The porous or grid-like polymer structure should allow the IV fluid to contact the interior surface of wall portions 11 and 36 to allow the beneficial agent to be delivered into the IV fluid. When the wall portions 11 and 36 are comprised of a fragile material or a material having poor tear strength, it may be necessary to provide a protective covering (not shown in the figures) thereover. The protective covering can take any number of forms but in any event should be effective to prevent or minimize unnecessary stresses placed on the wall portions 11 and 36 and yet provide easy access to attach a drug delivery device 40 thereon.

In its broadest sense, the drug delivery device 40 comprises a beneficial agent-containing reservoir which can be releasably attached to the exterior surface of the wall portion 11 and/or 36. Typically, the reservoir comprises a polymeric matrix having a drug or other beneficial agent dispersed therein. The reservoir may be releasably attached to the wall portions 11 and/or 36 using tape, clamps, adhesives or other conventional attaching means. Mechanical attaching means are preferred where the beneficial agent delivered by the device is incompatible with adhesives. In cases where the beneficial agent is adhesive-compatible, the reservoir preferably incorporates a releasable contact adhesive, or has a releasable contact adhesive layer coated on one side thereof, so that the reservoir is itself releasably adhered to the wall portion 11 and/or 36.

The agent delivery device 40 used in the present invention is not limited to any particular type or structure. Many suitable devices are known in the art and have generally been used in applications wherein a drug or other beneficial agent is administered transdermally. Examples of suitable agent delivery devices 40 may be found for example in U.S. Pat. Nos. 3,536,809; 3,598,122; 3,598,123; 3,787,571; 3,699,963; 3,731,683; 3,734,097; 3,742,951; 3,797,494; 3,964,482; 3,996,934; 4,031,894; 4,060,084; and others to name just a few. The teachings of the above listed patents concerning the relevant structures of the drug delivery devices and the particular drugs which may be suitably administered using these devices are incorporated herein by reference.

Figure 4:
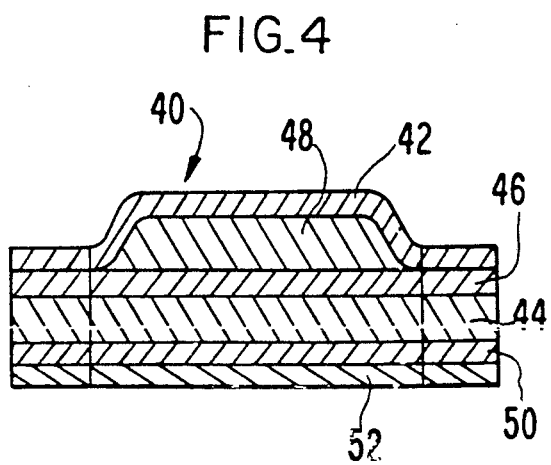
FIG. 4 is a detailed sectional view of a preferred drug delivery device 40 which is adapted to be attached to formulator 30 as shown in FIGS. 1-3.

A preferred drug delivery device 40 is illustrated in FIG. 4. Device 40 is a multilaminate system comprised of an impermeable backing layer 42, a drug reservoir 48 and an adhesive layer 50. Device 40 also includes a permeation enhancer-containing layer 44 (e.g., an ethanol gel layer) and a rate controlling membrane 46. A strippable release liner 52, adapted to be removed prior to application, is normally included in the packaged product.

The drug reservoir 48 may be comprised of a polymeric matrix or carrier having the drug/beneficial agent to be delivered, dispersed throughout. The polymer matrix stores and releases the beneficial agent/drug by diffusion or by osmotic action to wall portion 11 and/or 36. Representative polymers for forming the matrix may be selected from homopolymers, copolymers, cross-linked polymers, diffusion polymers and microporous polymers. Examples of suitable polymers include acrylic polymers and copolymers of methacrylate, ethylacrylate, ethylmethacrylate, and methylmethacrylate; homopolymers and copolymers including vinylchloride-vinylacetate copolymer; chlorinated vinyl chloride; polyethylene; polypropylene; ethylene-propylene copolymer; chlorinated polyethylene; ethylene-vinyl acetate copolymer (EVA) of the type described in U.S. Pat. No. 4,144,317; styrene-butadiene copolymer; acrylonitrile-styrene-butadiene terpolymer; polyvinylidene chloride; vinylchloride-acrylonitrile copolymer; vinylchloridevinylidene chloride copolymer; vinylidenechloride-acrylate ester copolymer; polybutylene terephthalate; vinylchloride-acrylate ester copolymer; cross-linked polyvinyl acetals such as cross-linked polyvinyl formal; cross-linked polyvinyl acetal and cross-linked polyvinyl butyral; polyethers; polyesters; sparingly cross-linked polyesters; polyurethane; polyamide; chlorosulfonated polyolefins; polyolefins; polybutadiene; polyisoprene; polysilicone; natural and synthetic rubbers; and the like. The polymers are known in *The Handbook of Common Polymers*, by Scott et al., (1971), published by CRC Press, Cleveland OH; in *Modern Plastics Encyclopedia*, (1979), published by McGraw-Hill Inc., New York, N.Y.; and in *Handbook of Plastics and Elastomers*, by Harper, (1976), published by McGraw-Hill Inc., San Francisco, Calif.

The drug reservoir 48 may contain the drug alone or it may contain the drug along with one or more permeation enhancers. The drug/beneficial agent should either itself be soluble in the parenteral fluid or be capable of being solubilized using adjuvants such as surfactants and/or co-ions. The amount of drug in the reservoir 48 will depend upon the rate at which the drug is delivered from the system and the intended duration of therapy. The amount of drug/beneficial agent in reservoir 48 generally will be about 0.1% to 80% by weight, with a more preferred amount of 5% to 50% by weight. The device 40 can be manufactured for delivering beneficial amounts of a drug over a prolonged period from about 0.5 hours to several days or longer, with a more preferred period of about 4 to 50 hours. The device 40 used in the present invention releases from 10 ng to 750 mg per hour, or higher. The reservoir 48 may also include diluents, stabilizers, vehicles, gelling agents, and the like.

The backing member 42 serves the purpose of insuring unidirectional passage of drug through wall portion 11 and/or 36 into container 12 and/or chamber 34, and also of providing support for the system, where needed. The backing layer can be flexible or nonflexible and suitable materials include, without limitation, cellophane, cellulose acetate, ethylcellulose, plasticized vinylacetatevinylchloride copolymers, polyethylene terephthalate, nylon, high and low density polyethylene, polypropylene, metalized polyester films, 6 polyvinylidene chloride, coated flexible fibrous backings such as paper and cloth and aluminum foil. Such backings can be in the form of precast films or fabrics which are bonded to the reservoir by heat or adhesives and can be coated onto the reservoir 48.

The device 40 is held in place on wall portion 11 and/or 36 by means of an in-line pharmaceutically acceptable contact adhesive layer 50. Drug and/or a permeation enhancer may also be incorporated into the adhesive layer 50. The composition and thickness of the adhesive layer 50 are preferably such that it does not constitute a significant permeation barrier to the drug or the permeation enhancer, if one is present Any pharmaceutically acceptable contact adhesive may be used. Representative adhesives include mixtures of 2-cyanoacrylate and dimethyl methylenemalonate, monomeric ester of alpha-cyanoacrylic acid, cross-linked copolymer of dimethylaminoethylmethacrylate and an alkyl acrylate, adhesive compositions comprising a hydrocolloid gum, polyisobutylene and cross-linked dextran, silicone medical adhesives, mineral oil-polyisobutylene adhesives, contact adhesives such as those disclosed in U.S. Pat. Nos. 3,797,494 and 4,031,894, and the like. The adhesive optionally can contain a rheological agent that imparts thixotropic characteristics to the adhesive, aids in increasing its cohesiveness and bond strength, imparts slump control, maintains the delivery device 40 in contact with wall portion 11 and/or 36, and lets it be easily removed therefrom at the end of the delivery period. The rheological agents useful for this purpose are silicon compounds such as fumed silica.

The adhesive may also optionally contain a surfactant which allows better contact between the surface of the delivery device 40 and the exterior surface of wall portion 11 and/or 36.

If necessary or desirable, known permeation enhancers, such as ethanol or glycerol monolaurate, may be contained either within the separate layer 44 (if one is present), in the adhesive layer 50, in the drug reservoir 48, or in any combination of these.

Most preferably, device 40 includes a rate controlling membrane 46 which is effective to control the rate at which the beneficial agent is delivered from reservoir 48 into container 12 and/or chamber 34. When device 40 contains a rate controlling membrane 46, the wall portions 11 and 36 should provide minimal resistance to drug flux. The rate controlling membrane 46 may be comprised of permeable, semipermeable or microporous materials which are known in the art to control the flux rate of the drug out of the device 40. Suitable materials include polyvinylacetate and ethylene vinylacetate polymers. When a rate controlling membrane 46 is present in device 40, the beneficial agent delivery rate is determined by the delivery device 40, and not by the wall portions 11 and 36.

However, it is also within the scope of the present invention to utilize a delivery device 40 containing no rate controlling membrane 46. When no rate controlling membrane 46 is provided in delivery device 40, the wall portion 11 and/or 36 should be comprised of a material which is effective to control the rate at which the beneficial agent is delivered into container 12 and/or chamber 34. When the wall portion 36 itself controls the rate at which the beneficial agent is delivered into chamber 34, the formulator 30 will be relatively drug specific (i.e., the formulator will only be suitable to control the rate of delivery of a specified drug or class of drugs). Likewise, when the wall portion 11 itself controls the rate at which the beneficial agent is delivered into the container 12, the container 12 will be relatively drug specific (i.e., the IV fluid container will only be suitable to control the rate of delivery of a specified drug or class of drugs.).

On the other hand, when the wall portion 36 provides minimal resistance/control over the drug flux therethrough, the formulator 30 can be used with a wide range of drugs. Similarly, when the wall portion 11 provides minimal resistance/control over the drug flux therethrough, the container 12 can be used with a wide range of drugs. However, in this second configuration, the control of drug delivery should be provided by the drug delivery device 40. This is preferred since transdermal type drug delivery devices are generally manufactured to deliver a specific drug at a specific drug delivery rate.

The size (e.g., the surface area of adhesive layer 50 which is in contact with wall portion 11 and/or 36) of the device 40 can typically vary from less than 1 cm$^2$ to greater than 200 cm$^2$. An average device 40 however, will typically have a size within the range of about 5-50 cm$^2$.

Embodiments of device 40 in which the drug and permeation enhancer supplies are separate (such as that illustrated in FIG. 4) may be advantageous or necessary in instances where formulation or storage of the drug and the enhancer in contact with each other is impractical or undesirable or where separation of the drug and the enhancer facilitates selection of the rate controlling membrane.

The size (i.e., the surface area) of wall portions 11 and 36 should be large enough to accommodate at least one delivery device 40, and preferably large enough to accommodate two or more delivery devices 40. By making wall portions 11 and 36 large enough to accommodate a plurality of the delivery devices 40, it is possible to simultaneously deliver more than one beneficial agent into the IV fluid 13. Likewise, it is also possible to deliver a single beneficial agent at a delivery rate which is a multiple (e.g., 2×, 3×, 4×, etc.) of the delivery rate achieved by a single delivery device 40 (e.g., by adhering 2, 3, 4, etc. identical devices 40 to wall portions 11 and/or 36).

Important advantages achieved by the container 12 and the formulator 30 of the present invention include (1) easy adjustment of the beneficial agent delivery rate, (2) easily changing the type of beneficial agent delivered, (3) it is unnecessary for a nurse or a pharmacist to preformulate the drug or other beneficial agent and (4) the drug or other beneficial agent has a longer stable shelf-life since the drug is maintained in a solid, rather than in solution, form. For instance, if it is desired to increase the rate of delivery of a beneficial agent (e.g., an antibiotic) into the flowing IV fluid 13, one can simply select a suitable antibiotic delivery device 40 with a specified delivery rate. Furthermore, if it is desired to either double, triple or quadruple the delivery rate of this particular antibiotic, it is only necessary to apply 2, 3, or 4 delivery devices 40, respectively, to the wall portions 11 and/or 36.

Likewise, if instead of delivering an antibiotic it is desired to deliver an anti-cancer agent into the flowing IV fluid, it is only necessary to remove the antibiotic-containing drug delivery device 40 and replace it with an anti-cancer drug-containing delivery device.

Because the agent delivery devices 40 are attached to the exterior surfaces of container 12 and formulator 30, there is no danger of contamination of the flowing IV fluid. Thus, changing the type of drug delivered or the drug delivery rate does not require time consuming sterilization procedures. This is especially important when utilizing devices which deliver protein formulations since proteins are sensitive to heat sterilization and have a tendency to denature when heated.

Other benefits and advantages of the invention will become apparent to those skilled in the art While the preferred embodiments of the invention have been selected for illustration in the drawings and have been described in detail herein, those skilled in the art will appreciate that various modifications, changes, additions and omissions from the illustrated embodiments can be made without departing from the spirit and scope of the invention, as defined in the appended claims.

We claim:

1. A parenteral delivery system for administering an agent parenterally to an animal in which the agent is formulated in situ, comprising in combination:
   (1) a container of a pharmaceutically acceptable parenteral fluid that is a carrier for the agent;
   (2) a parenteral fluid administration set connected to the container for permitting the fluid to flow from the container through the administration set to the animal, the set comprising a drip chamber, tubing extending from the drip chamber to the animal, and an agent formulator connected into the tubing such that the intravenous fluid flows through the formulator;
   the formulator comprising:
      (a) a chamber having fluid inlet and outlet means to maintain a continuous flow of the parenteral fluid therethrough, the chamber having a wall portion that (1) is permeable to the beneficial agent to be delivered into the fluid and (2) prevents convective flow of parenteral fluid therethrough, the wall portion having an interior surface and an exterior surface which is accessible from the exterior of the formulator;
(b) a flow distributor within the chamber for distributing the flow of parenteral fluid along the interior surface of the wall portion; and
(c) a transdermal-type agent delivery device attached to the external surface of the wall portion, the delivery device comprising a reservoir containing the beneficial agent, the reservoir being releasably attached to the external surface of the portion;
wherein in operation, the fluid flowing through the chamber is directed by the flow distributor to flow along the internal surface of the wall portion, causing the agent to be delivered from the device through the wall portion and into the flowing fluid, the agent being delivered at a rate which is controlled substantially by the formulator and which is substantially independent of volumetric flow rate of the fluid flowing through the chamber.

2. The parenteral delivery system of claim 1, wherein the delivery device comprises a laminate including: (1) a backing member, (2) a middle reservoir containing the beneficial agent, and (3) an adhesive surface adapted to releasably adhere to the external surface of the wall portion.

3. The parenteral delivery system of claim 1, wherein a skin piercing means is connected to the tubing for administering the agent to the animal.

4. The parenteral delivery system of claim 1, wherein the animal is a human and the agent comprises a drug.

5. The parenteral delivery system of claim 1, wherein the parenteral fluid is an intravenously acceptable fluid.

6. The parenteral delivery system of claim 1, wherein the delivery device is releasably adhered to the external surface of the wall portion.

7. The parenteral delivery system of claim 1, wherein the chamber is cylindrically shaped and said wall portion extends around the entire circumference of the chamber.

8. The parenteral delivery system of claim 7, wherein the flow distributor comprises a cylindrically shaped member fixedly positioned within the chamber.

9. The parenteral delivery system of claim 1, wherein the flow distributor channels the parenteral fluid flow into a constricted space between the distributor and the wall portion.

10. A parenteral fluid reservoir container for use in a parenteral fluid delivery system, the container comprising:
(a) a chamber for containing the parenteral fluid and having fluid outlet means to provide a continuous flow of the parenteral fluid out of the container, the chamber having a wall portion comprised of a material that (1) is permeable to a beneficial agent to be delivered into the fluid and (2) prevents convective flow of parenteral fluid therethrough, the wall portion having an interior surface and an exterior surface which is accessible from the exterior of the container; and
a transdermal-type agent delivery device attached to the exterior surface of the wall portion, the delivery device comprising a reservoir containing the beneficial agent, the reservoir being releasably attached to the exterior surface of the wall portion;
wherein in operation, the fluid in the container contacts an interior surface of the wall portion, causing the agent to be delivered from the device through the wall portion and into the fluid, the agent being delivered at a rate which is controlled substantially by the wall portion or by the agent delivery device and which is substantially independent of volumetric flow rate of the fluid flowing out of the container.

11. The container of claim 10, wherein the delivery device comprises a laminate including: (1) a backing member, (2) a middle reservoir containing the beneficial agent, and (3) an adhesive surface adapted to releasably adhere to the external surface of the wall portion.

12. The container of claim 10, wherein the parenteral fluid is an intravenously acceptable fluid.

13. The container of claim 10, wherein the animal is a human and the agent comprises a drug.

14. The container of claim 12, wherein the rate at which the agent is delivered into the chamber is controlled by the wall portion.

15. The container of claim 10, wherein the delivery device includes a membrane interposed between the beneficial agent reservoir and the wall portion, the membrane controlling the rate at which the delivery device delivers the beneficial agent into the chamber.

16. The container of claim 10, wherein the wall portion is comprised of a solution-diffusion membrane.

17. The container of claim 10, wherein the wall portion is comprised of a microporous membrane.

18. The container of claim 10, wherein the wall portion has a size and shape enabling a plurality of agent delivery devices to be attached to the exterior surface thereof.

19. The container of claim 10, wherein the delivery device is releasably adhered to the wall portion.

20. The container of claim 10, wherein the agent is osmotically active.

21. The container of claim 10, wherein the agent comprises a drug and an osmotically active solute.

* * * * *